United States Patent
Chabrier De Lassauniere et al.

(10) Patent No.: US 6,770,669 B1
(45) Date of Patent: Aug. 3, 2004

(54) AMIDINE DERIVATIVES, PREPARATION AND USE THEREOF AS MEDICINES

(75) Inventors: Pierre-Etienne Chabrier De Lassauniere, Paris (FR); Jeremiah Harnett, Gif-sur-Yvette (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 10/111,434
(22) PCT Filed: Nov. 15, 2000
(86) PCT No.: PCT/FR00/03168
§ 371 (c)(1), (2), (4) Date: Apr. 23, 2002
(87) PCT Pub. No.: WO01/36407
PCT Pub. Date: May 25, 2001

(30) Foreign Application Priority Data

Nov. 16, 1999 (FR) .......................................... 99 14334

(51) Int. Cl.⁷ .............................................. A61K 31/38
(52) U.S. Cl. ..................................................... 514/438
(58) Field of Search ............................. 514/438; 549/74

(56) References Cited

U.S. PATENT DOCUMENTS 5,807,885 A * 9/1998 Gentile et al. .............. 514/438

6,340,700 B1   1/2002 Chabriere de Lassauniere et al.

FOREIGN PATENT DOCUMENTS

| EP | 0798292 | 10/1997 |
|---|---|---|
| WO | 9505363 | 2/1995 |
| WO | 9618607 | 6/1996 |
| WO | 9746515 | 12/1997 |

* cited by examiner

Primary Examiner—Deborah C. Lambkin
(74) Attorney, Agent, or Firm—Muserlian, Lucas and Mercanti

(57) ABSTRACT

A seat adjustment mechanism is provided and includes an arm defining a first locking shoulder, a sector plate rotatably supported by the arm and defining a second locking shoulder having a lock recess, a locking member selectively engaging at least one of the first and second locking shoulders, a quadrant rotatably supported by the arm and slidably supporting the locking member for locking the quadrant in one of a first and second position relative to the arm and a cam plate rotatably supported by the quadrant for selectively engaging the locking member for locking the quadrant in one of the first and second positions. In the first position the locking member is biased against the first locking shoulder and in the second position the locking member is biased into the lock recess. A gear assembly is preferably provided and operably supported by the quadrant for actuation of the cam plate.

6 Claims, No Drawings

AMIDINE DERIVATIVES, PREPARATION AND USE THEREOF AS MEDICINES

This application is a 371 of PCT/FR00/03168 filed Nov. 15, 2000.

The present invention relates to new derivatives of amidines, their preparation and their use as medicaments. It relates in particular to the use of said derivatives for preparing a medicament intended to inhibit NO synthases (NOS) and/or monoamine oxydases (MAO).

Taking into account the potential role of NOS and MAO in physiopathology, the new described derivatives corresponding to general formula (I) can produce beneficial or favourable effects in the treatment of pathologies where these two enzymes are involved. In particular the following pathologies are involved.

disorders of the central or peripheral nervous system such as for example neurological diseases where Parkinson's disease, cerebral or spinal cord traumatisms, cerebral infarction, sub arachnoid hemorrhage, epilepsy, ageing, senile dementia, Alzheimer's disease, Huntington's chorea, amyotrophic lateral sclerosis, peripheral neuropathies, pain;

schizophrenia, depressions, psychoses;

disorders of the memory and the humour;

pathologies such as for example migraine;

behavioural disorders, boulimia and anorexia;

auto-immune and viral diseases such as for example lupus, AIDS, parasitic and viral infections, diabetes and its complications (in particular impotence linked to diabetes), multiple sclerosis;

addiction to toxic substances;

proliferative and inflammatory pathologies;

and more generally all the pathologies characterized by an excessive production of NOS and/or participation by MAO.

In all of these pathologies, experimental evidence exists which demonstrates the involvement of NOS (*J. Med. Chem.* (1995) 38, 4343–4362) as well as the involvement of MAO (Goodman & Gilman's: *The pharmacological hosts of therapeutics*, 9th ed., 1995, 431–519).

The inventors have already described inhibitors of NO Synthases and their use in previous patents (U.S. Pat. Nos. 5,081,148; 5,360,925). The PCT Patent Application WO 95/05363 describes certain derivatives of amidines and their use as inhibitors of NO synthases. The Applicant has itself described more recently other derivatives of amidines, which inhibit NO synthases and/or trap the reactive oxygen species (ROS for *Reactive Oxygen Species*) (cf. in particular PCT Patent Applications WO 98/42696 and WO 98/58934).

The Applicant has just now discovered that, surprisingly, the derivatives of amidines corresponding to general formula (I) defined hereafter are inhibitors of NOS and/or MAO.

The compounds of the invention correspond to the general formula (I)

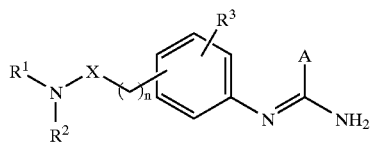

(I)

in which:

R$^1$ and R$^2$ represent, independently, a hydrogen atom or an alkyl, cycloalkyl, alkenyl, alkynyl, allenyl, allenylalkyl, cyanoalkyl, —(CH$_2$)$_g$—Z$^1$R$^4$ or —(CH$_2$)$_k$—COR$^5$ radical, Z$^1$ representing —O—, —NR$^6$—, —S— or a bond, R$^4$ and R$^6$ representing, independently, a hydrogen atom or an alkyl, alkenyl, allenylalkyl, alkynyl, alkoxy or cyanoalkyl radical, R$^5$ representing an alkyl, allenyl, allenylalkyl, alkenyl, alkynyl, cyanoalkyl, alkoxy or NR$^7$R$^8$ radical, R$^7$ and R$^8$ representing, independently, a hydrogen atom or an alkyl, allenyl, allenylalkyl, alkenyl, alkynyl, cyanoalkyl or alkoxy radical, or R$^1$ and R$^2$ together with the nitrogen atom form a non-aromatic heterocycle with 4 to 8 members, the elements of the chain being chosen from a group comprising —CH(R$^9$)—, —NR$^{10}$—, —O—, —S—, —CO—, said heterocycle being able to be substituted by one or more substituents —(CH$_2$)$_k$—Z$^2$R$^{11}$ or —(CH$_2$)$_k$—COR$^{12}$, said heterocycle being able to be for example an azetidine, a piperazine, a homopiperazine, a 3,5-dioxopiperazine, a piperidine, a pyrrolidine, a morpholine or a thiomorpholine, Z$^2$ representing —O—, —NR$^{13}$— or —S— or a bond, R$^{11}$, each time that it occurs, representing independently a hydrogen atom, an alkyl, alkenyl, alkynyl, alkoxy, allenyl, allenylalkyl or cyanoalkyl radical, R$^{13}$, each time that it occurs, representing, independently, a hydrogen atom or an alkyl, alkenyl, alkynyl, alkoxy, allenyl, allenylalkyl or cyanoalkyl radical, R$^{12}$, each time that it occurs, representing an alkyl, allenyl, allenylalkyl, alkenyl, alkynyl, cyanoalkyl, or alkoxy or NR$^{14}$R$^{15}$ radical, R$^{14}$ and R$^{15}$, each time that they occur, representing, independently, a hydrogen atom or an alkyl, alkoxy, allenyl, allenylalkyl, alkenyl, alkynyl or cyanoalkyl radical, R$^9$ and R$^{10}$, each time that they occur, representing independently a hydrogen atom, —(CH$_2$)$_k$—Z$^3$R$^{16}$ or —(CH$_2$)$_k$COR$^{17}$, Z$^3$ representing —O—, —NR$^{18}$—, —S— or a bond, R$^{18}$ representing, independently, a hydrogen atom or an alkyl, alkenyl, allenyl, allenylalkyl, alkynyl, alkoxy or cyanoalkyl radical, R$^{16}$, each time that it occurs, representing independently a hydrogen atom or an alkyl, alkenyl, alkynyl, alkoxy, allenyl, allenylalkyl or cyanoalkyl radical, R$^{17}$, each time that it occurs, representing independently an alkyl, allenyl, allenylalkyl, alkenyl, alkynyl, cyanoalkyl, alkoxy or NR$^{19}$R$^{20}$ radical, R$^{19}$ and R$^{20}$ representing, independently, each time that they occur, a hydrogen atom or an alkyl alkoxy, allenyl, allenylalkyl, alkenyl, alkynyl or cyanoalkyl radical;

X represents a —CO— or —(CH$_2$)$_m$— radical;

R$^3$ represents a hydrogen atom or a linear or branched alkyl or alkoxy radical having 1 to 6 carbon atoms;

A represents a linear or branched alkyl radical having 1 to 6 carbon atoms or a carbocyclic or heterocyclic aryl radical with 5 or 6 members containing 1 to 4 heteroatoms chosen from O, S, N and in particular the thiophene, furane, pyrrole or thiazole radicals, said aryl radical being optionally substituted by one or more groups chosen from the linear or branched alkyl, alkenyl or alkoxy radicals having 1 to 6 carbon atoms, g, each time that it occurs, representing, independently, an integer from 1 to 6, m, k and n, each time that they occur, representing, independently, integers from 0 to 6;

it being understood however that, when R³ represents a hydrogen atom or a linear or branched alkyl radical having 1 to 6 carbon atoms, then R¹ and R² do not represent, independently, a hydrogen atom or an alkyl radical, and moreover NR¹R² do not represent one of the non substituted piperidinyl, morpholinyl, pyrrolidinyl groups or the piperazinyl group optionally substituted in position 4 by an alkyl radical containing 1 to 6 carbon atoms.

By alkyl, when it is not specified otherwise, is meant a linear or branched alkyl radical containing 1 to 6 carbon atoms. By cycloalkyl, when it is not specified otherwise, is meant a monocyclic carbon system containing 3 to 7 carbon atoms. By alkenyl, when it is not specified otherwise, is meant a linear or branched alkyl radical containing 1 to 6 carbon atoms and having at least one unsaturation (double bond). By alkynyl, when it is not specified otherwise, is meant a linear or branched alkyl radical containing 1 to 6 carbon atoms and having at least one double unsaturation (triple bond). By allenyl, is meant the —CH=C=CH₂ radical. By carbocyclic or heterocyclic aryl, is meant a carbocyclic or heterocyclic system comprising at least one aromatic ring, a system being called heterocyclic when at least one of the rings which comprise it contains a heteroatom (O, N or S). By heterocycle, is meant a mono- or polycyclic system said system comprising at least one heteroatom chosen from O, N and S and being saturated, partially or totally unsaturated or aromatic. By haloalkyl, is meant an alkyl radical of which at least one of the hydrogen atoms (and optionally all) are replaced by a halogen atom.

By alkylthio, alkoxy, haloalkyl, haloalkoxy, aminoalkyl, alkenyl, alkynyl, cyanoalkyl and aralkyl radicals, is meant respectively the alkylthio, alkoxy, haloalkyl, haloalkoxy, aminoalkyl, alkenyl, alkynyl, cyanoalkyl and aralkyl radicals of which the alkyl radical has the meaning indicated previously.

By heterocycle, is meant in particular the thiophene, pyrrole, pyrrolidine, furane, tetrahydrofuran, piperidine, piperazine, quinoline, indoline and indole radicals. By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. Finally, by halogen, is meant the fluorine, chlorine, bromine or iodine atoms.

In certain cases, the compound according to the present invention can contain asymmetrical carbon atoms. As a result, the compounds according to the present invention have two possible enantiomeric forms, i.e. the "R" and "S" configurations. The present invention includes the two enantiomeric forms and all combinations of these forms, including the racemic "RS" mixtures. In an effort to simplify matters, when no specific configuration is indicated in the structural formulae, it should be understood that the two enantiomeric forms and their mixtures are represented.

The invention relates in particular to the products of general formula (I) defined previously, in which, independently, at least one of the following characteristics is found:

R¹ representing an alkyl radical and R² representing one of the alkyl, cycloalkyl, alkenyl, alkynyl, allenyl, allenylalkyl, cyanoalkyl, —(CH₂)$_g$—Z¹R⁴ or —(CH₂)$_k$—COR⁵ radicals as defined above;

R¹ and R² together with the nitrogen atom forming a non-aromatic heterocycle with 4 to 8 members, the elements of the chain being chosen from a group comprising —CH(R⁹)—, —NR¹⁰— and —O—, R⁹ and R¹⁰ representing independently a hydrogen atom or a —(CH₂)$_k$—Z³R¹⁶ or —(CH₂)$_k$COR¹⁷ radical, Z³ representing a bond, R¹⁶ representing independently a hydrogen atom, an alkyl, alkenyl, alkynyl, allenyl, allenylalkyl or cyanoalkyl radical, R¹⁷ representing independently an alkyl, allenyl, allenylalkyl, alkenyl, alkynyl or cyanoalkyl radical;

n representing 0 or 1;

k representing an integer from 1 to 6;

X representing —(CH₂)$_m$— with m representing 0 or 1.

More preferably, the products of general formula (I) defined previously, such that, independently, at least one of the following characteristics is found:

R¹ representing an alkyl radical and R² representing one of the alkyl, alkenyl, alkynyl, allenyl, allenylalkyl or cyanoalkyl radicals;

R¹ and R² together with the nitrogen atom form a non-aromatic heterocycle with 4 to 8 members, the elements of the chain being chosen from a group comprising —CH(R⁹)— and —NR¹⁰—, R⁹ and R¹⁰ representing independently a hydrogen atom or a —(CH₂)$_k$—Z³R¹⁶ radical, Z³ representing a bond, R¹⁶ representing independently a hydrogen atom or an alkyl, alkynyl or cyanoalkyl radical;

n representing 0 or 1;

k representing an integer from 1 to 3;

X representing —(CH₂)$_m$— with m representing 0 or 1;

The particularly preferred products of general formula (I) are:

N'-(4-{[methyl-(2-propynyl)amino]methyl}phenyl)-2-thiophenecarboximidamide;

N'-(4-{[methyl(cyanomethyl)amino]methyl}phenyl)-2-thiophenecarboximidamide;

N'-(4-{[methyl(propyl)amino]methyl}phenyl)-2-thiophenecarboximidamide;

N'-(4-{[methyl(3-cyanoethyl)amino]methyl}phenyl)-2-thiophenecarboximidamide;

N'-(4-{[methyl(4-pentynyl)amino]methyl}phenyl)-2-thiophenecarboximidamide;

and the salts of the latter.

Finally, N'-(4-{[methyl-(2-propynyl)amino]methyl}phenyl)-2-thiophene carboximidamide or the salts of the latter are particularly preferred.

The invention also relates, as medicaments, to the compounds of general formula (I) or their pharmaceutically acceptable salts. In addition, a subject of the invention is the pharmaceutical compositions containing, as active ingredient, a compound of general formula (I) or a pharmaceutically acceptable salt of a compound of general formula (I), as well as the use of the compounds of general formula (I) for preparing a medicament intended to inhibit NO synthases and/or monoamine oxydases, in particular monoamine oxydase B.

In particular, the compounds of general formula (I) can be used for preparing a medicament intended to treat one of the following disorders or one of the following diseases: Parkinson's disease, senile dementia, Alzheimer's disease, Huntington's chorea, amyotrophic lateral sclerosis, schizophrenia, depression, psychoses.

By pharmaceutically acceptable salt, is meant in particular the addition salts with inorganic acids such as hydrochloride, hydrobromide, hydroiodide, sulphate, phosphate, diphosphate, and nitrate or with organic acids such as acetate, maleate, fumarate, tartrate, succinate, citrate, lactate, methanesulphonate, p-toluenesulphonate, pamoate, and stearate. Also included in the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201–217.

The pharmaceutical composition can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or glycols, similarly their mixtures, in varying proportions, in water.

The administration of a medicament according to the invention can be done by topical, oral, parenteral route, by intramuscular injection, etc.

The administration dose envisaged for a medicament according to the invention is comprised between 0.1 mg to 10 g according to the type of active compound used.

In accordance with the invention, the compounds of general formula (I) can be prepared by the processes described below.

PREPARATION OF THE COMPOUNDS OF THE INVENTION

The compounds of general formula (I) can be prepared from the intermediates of general formula (II) according to Diagram 1 where A, X, $R^1$, $R^2$, $R^3$ and n are as defined above and Gp is a protective group of carbamate type.

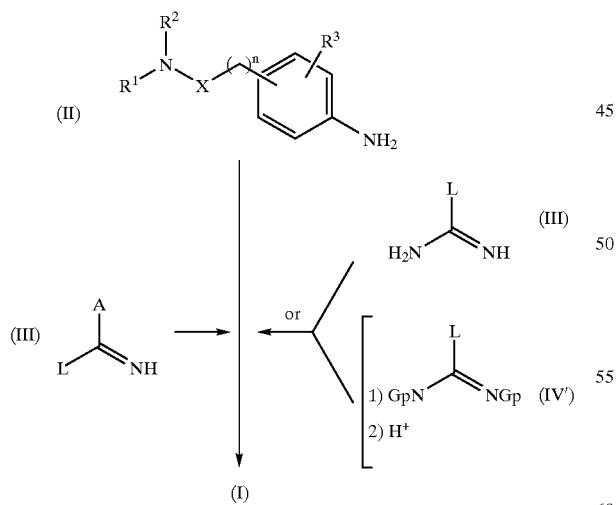

The derivatives of anilines of general formula (II), can be condensed with the compounds of general formula (III), in which L represents a parting group (an alkoxy, alkylthio, sulphonic acid, halide, aryl alcohol or tosyl radical), in order to produce the final compounds of general formula (I) of substituted amidine type (cf. Diagram 1). For example, for A=thiophene, the derivatives of general formula (II) can be condensed with S-methylthiophene thiocarboxamide hydroiodide, prepared according to a method in the literature (*Ann. Chim.* (1962), 7, 303–337). The condensation can be carried out by heating in an alcohol (for example in methanol or isopropanol), optionally in the presence of DMF at a temperature preferably comprised between 50 and 100° C. for a duration generally comprised between a few hours and overnight.

In the case where A is an amine, the final compounds of general formula (I) are guanidines. These can be prepared, for example, by the condensation of the amines of general formula (II) with the derivatives of general formula (IV) or (IV'). The reagents of general formula (IV), in which L represents, for example, a pyrazole ring, are condensed with the anilines of general formula (II) according to conditions described in the literature (*J. Org. Chem.* (1992) 57, 2497–2502). The operation is carried out similarly for the reagents of general formula (IV') in which L represents, for example, a pyrazole ring and Gp the tBuOCO group (*Tetrahedron Lett.* (1993) 34 (21), 3389–3392) or when L represents the —N—SO₂—CF₃ group and Gp the tBuOCO group (*J. Org. Chem.* (1998) 63, 3804–3805). During the last stage of the synthesis, the deprotection of the guanidine function is carried out in the presence of a strong acid such as for example trifluoroacetic acid.

Preparation of the Compounds of General Formula (II)

The intermediates of general formula (II), are obtained, for example, from the reduction of a precursor of nitro type, as illustrated in synthesis Diagram 2 below.

Reduction of the Precursors of Nitro Type:

The reduction of the nitro function of the intermediates of general formula (V), Diagram 2, in which $R^1$, $R^2$, $R^3$, X and n and are as defined above, is generally carried out by catalytic hydrogenation, in ethanol, in the presence of Pd/C, except in the case of molecules which are sensitive to these conditions where the nitro group is selectively reduced, for example, while heating the product in an appropriate solvent such as ethyl acetate with a little ethanol in the presence of SnCl₂ (*J. Heterocyclic Chem.* 1987), 24, 927–930; *Tetrahedron Letters* (1984), 25 (8), 839–842) in the presence of SnCl₂/Zn (*Synthesis.* (1996), 9, 1076–1078) or using NaBH₄—BiCl₃ (*Synth. Com.* (1995) 25 (23), 3799–3803) in a solvent such as ethanol, or then by using Rancy Ni with hydrazine hydrate added to it (*Monatshefte für Chemie*, (1995), 126, 725–732).

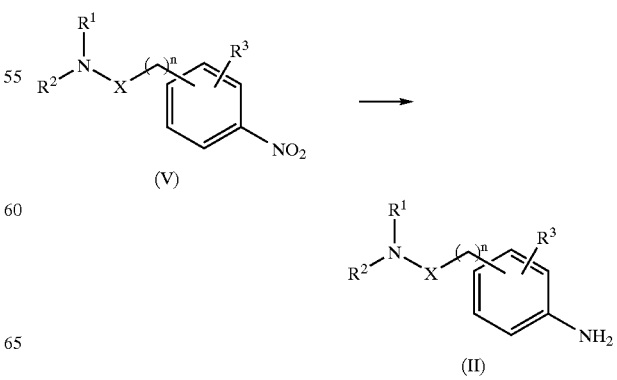

Preparation of the Compounds of General Formula (V)

Syntheses of the Carboxamides:

The carboxamides of general formula (V), Diagram 3, in which $R^1$, $R^2$, $R^3$, m and n are as defined above, are prepared by condensation of the acids of general formula (VI) with the amines of general formula (VII) (Diagram 3) or of the acids of the general formula (VIII) with of the amines of general formula (IX) (Diagram 3a) under standard conditions for peptide synthesis (M. Bodanszky and A. Bodanszky, The Practice of Peptide Synthesis, 145 (Springer-Verlag, 1984)) in particular in THF, dichloromethane or DMF in the presence of a coupling reagent such as dicyclohexylcarbodiimide (DCC), 1,1'-carbonyldiimidazole (CDI) (J. Med. Chem. (1992), 35 (23), 4464–4472) or 1-(3-dimethylaminopropyl)-3-ethylcarbodiimide hydrochloride (EDC or WSCI) (John Jones, The chemical synthesis of peptides, 54 (Clarendon Press, Oxford, 1991)).

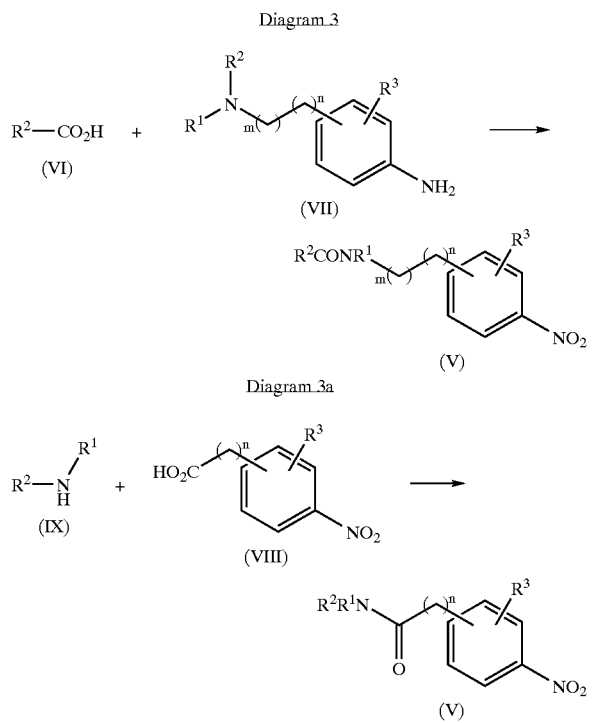

Synthesis of the Amines of General Formula (V):

The amines of general formula (V), Diagram 4, in which $R^1$, $R^2$, $R^3$, m and n as defined above, can be prepared in a single stage by condensation of the amines of general formula (VII) with the halogenated derivatives of general formula (X) (Hal represents a halogen atom) in the presence of a base such as, for example, $K_2CO_3$ and/or triethylamine, in a solvent such as, for example, acetonitrile.

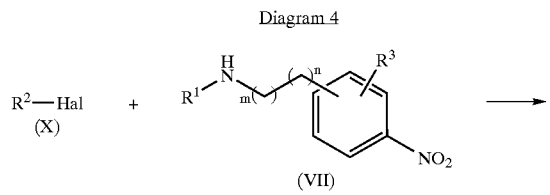

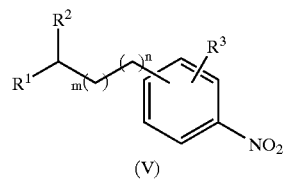

When $R^1$, $R^2$, $R^3$, m and n are as defined above, the amines of general formula (V) can also be prepared from the halogenated derivatives of formula (XI) (Hal represents a halogen atom) and the amines of general formula (IX), Diagram 5, in the presence of a base such as, for example, $K_2CO_3$ and/or triethylamine, in a solvent such as, for example, acetonitrile.

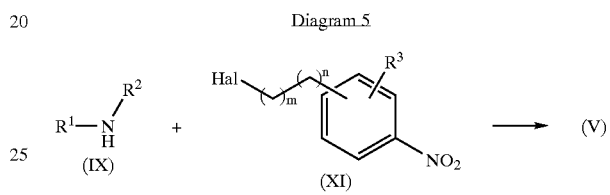

Synthesis of the Amines by Reducing Amination:

The amines of general formula (V), Diagram 6, in which $R^1$, $R^2$, $R^3$, m and n are as defined above, can be prepared by condensation of an aldehyde of general formula (XII) with an amine of general formula (VII) in a reducing medium. The reaction takes place in an alcoholic solvent such as, for example, methanol in the presence of a pulverulent 4 Å molecular sieve, activated beforehand, and of a reducing agent such as, for example, $NaBH_4$ or $NaBH_3CN$.

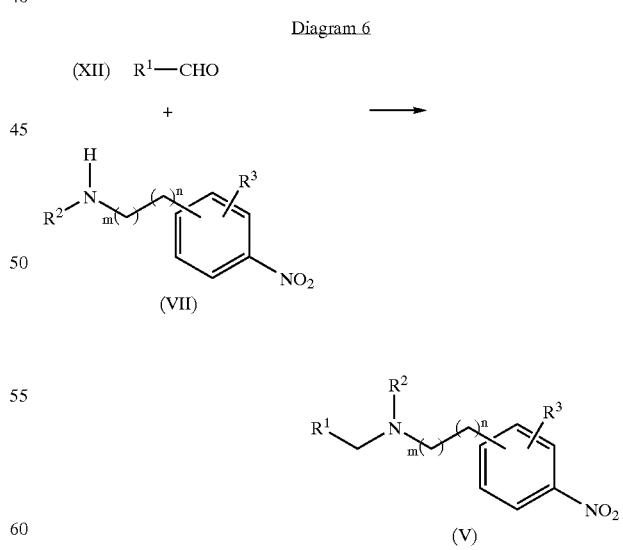

The amines of general formula (V), Diagram 7, in which $R^1$, $R^2$, $R^3$ and n are as defined above, can also be prepared by condensation of an amine of general formula (IX) with an aldehyde of general formula (XIII) in a reducing medium under the conditions described previously.

Diagram 7

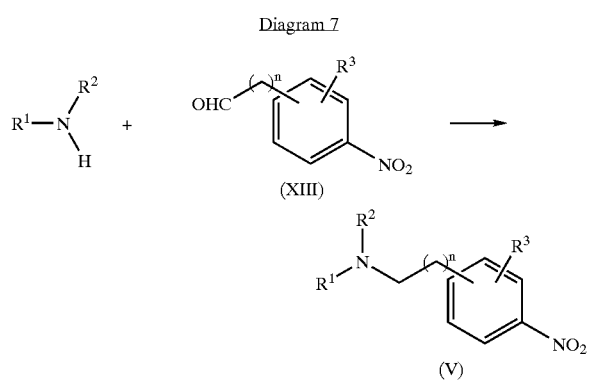

Unless otherwise defined, all the technical and scientific terms used here have the same meanings as those generally understood by an ordinary specialist in the field to which this invention belongs. Similarly, all the publications, patent applications, all patents and all other references mentioned here are incorporated by way of reference.

The following examples are presented in order to illustrate the above procedures and should in no event by considered as a limit to the scope of the invention.

EXAMPLES

Example 1

N'-(4-{[methyl(2-propynyl)amino]methyl}phenyl)-2-thiophenecarboximidamide 1.1. N-methyl-N-(4-nitrobenzyl)-2-propyn-1-amine 3.72 g (22.0 mmol) of p-nitrobenzyl chloride in 20 ml of dichloromethane is added, dropwise, at 0° C. to a solution of 1 g (1.45 mmol) of N-methylpropargylamine in 15 ml of dichloromethane and 3.1 ml of triethylamine. After stirring overnight, the reaction mixture is concentrated to dryness under vacuum, and the residue is diluted with dichloromethane and 40 ml of a saturated solution of NaCl. After stirring and decanting, the organic phase is separated and dried over magnesium sulphate, filtered and concentrated under vacuum. The expected product is obtained after chromatography on a silica column, eluent: (20% ethyl acetate in heptane), the pure fractions, after evaporation, produce a brown solid with a yield of 80%. Melting point 47–49° C.

MH+=205.20.

1.2. 4-{[methyl(2-propynyl)amino]methyl}aniline 1.4 g (6.11 mmoles) of $SnCl_2$, $2H_2O$ and 0.4 g (6.11 mmol) of Zn are added successively to a solution of 0.5 g (2.442 mmol) of intermediate 1.1 in a mixture of 12.0 ml of glacial acetic acid and 1.5 ml of HCl (12 N). The mixture is stirred for 18 hours at 20° C. The reaction mixture is then rendered basic by adding a 30% aqueous solution of NaOH. The product is then extracted using twice 50 ml of $CH_2Cl_2$. The organic solution is washed with 50 ml of salt water, dried over $MgSO_4$, filtered and concentrated under vacuum. A pale yellow oil is obtained with a yield of 90%. The residue is used without other purification in the following stage.

MH+=175.10.

1.3. N'-(4-{[methyl(2-propynyl)amino]methyl}phenyl)-2-thiophenecarboximidamide 0.315 g (1.80 mmol) of intermediate 1.2 and 0.77 g (2.70 mmol) of S-methyl-2-thiophenethiocarboximide hydroiodide is dissolved in 15 ml of isopropanol in a 25 ml flask. The reaction mixture is stirred for 20 hours at a temperature of 80° C. After evaporation of the solvent under vacuum, the residue is taken up in 25 ml of a mixture (1/1) of a saturated solution of $NaHCO_3$ and dichloromethane. After decanting, the organic phase is washed with 2×25 ml of salt water. The organic solution is dried over magnesium sulphate, filtered, concentrated under vacuum and the residue is purified on a silica gel column (eluent: dichloromethane+3% of ethanol). The pure fractions are collected and concentrated under vacuum. A white solid is obtained with a yield of 38%. Melting point: 109–110° C.

MH+=284.10.

The following compounds can be prepared according to a similar protocol to that described in Example 1.

Example 2

N'-(4-{[methyl(cyanomethyl)amino]methyl}phenyl)-2-thiophenecarboximidamide (N-methylpropargylamine is replaced by methylaminoacetonitrile in the first stage)

Example 3

N'-(4-{[methyl(propyl)amino]methyl}phenyl)-2-thiophenecarboximidamide (N-methylpropargylamine is replaced by N-methyl-N-propylamine in the first stage)

Example 4

N'-(4-{[methyl(3-cyanoethyl)amino]methyl}phenyl)-2-thiophenecarboximidamide (N-methylpropargylamine is replaced by N-methyl-β-alaninenitrile in the first stage)

Example 5

N'-(4-{[methyl(4-pentynyl)amino]methyl}phenyl)-2-thiophenecarboximidamide (N-methylpropargylamine is replaced in the first stage by N-methyl-N-pent-4-ynylamine (prepared according to *Tetrahedron Letters* (1992), 33(45), 6835–6838, and *Heterocycles* (1996), 42(1), 385–396))

Pharmacological Study of the Products of the Invention

Study of the Effects on Neuronal Constitutive NO Synthase of a Rat's Cerebellum

The inhibitory activity of the products of the invention is determined by measuring their effects on the conversion by NO synthase of [$^3$H]L-arginine to [$^3$H]L-citrulline according to the modified method of Bredt and Snyder (*Proc. Natl. Acad. Sci. USA.* (1990) 87: 682–685). The cerebellums of Sprague-Dawley rats (300 g—Charles River) are rapidly removed, dissected at 4° C. and homogenized in a volume of extraction buffer (HEPES 50 mM, EDTA 1 mM, pH 7.4, pepstatin A 10 mg/ml, leupeptin 10 mg/ml). The homogenates are then centrifuged at 21000 g for 15 min at 4° C. Dosage is carried out in glass test tubes in which 100 μl of incubation buffer containing 100 mM of HEPES (pH 7.4), 2 mM of EDTA, 2.5 mM of $CaCl_2$, 2 mM of dithiotreitol, 2 mM of reduced NADPH and 10 μg/ml of calmodulin are distributed. 25 μl of a solution containing 100 nM of [$^3$H]L-arginine (Specific activity: 56.4 Ci/mmole, Amersham) and 40 μM of non-radioactive L-arginine is added. The reaction is initiated by adding 50 μl of homogenate, the final volume being 200 μl (the missing 25 μl are either water or the tested product). After 15 min, the reaction is stopped with 2 ml of stopping buffer (20 mM of HEPES, pH 5.5, 2 mM of EDTA). After passing the samples through a 1 ml column of DOWEX resin, the radioactivity is quantified by a liquid scintillation spectrometer. The compound of Example 1 described above shows an $IC_{50}$ lower than 3.5 μM.

Study of the Effects on the Bond of a Specific Ligand of MAO-B, [$^3$H]Ro 19-6327

The inhibitory activity of the products of the invention is determined by measuring their effects on the bond of a specific ligand of MAO-B, [$^3$H]Ro 19-6327.

A) Mitochondrial Preparation of the Cortex of Rats

The mitochondrial preparation of the cortex of rats is carried out according to the method described in Cesura A M, Galva M D, Imhof R and Da Prada M, *J. Neurochem.* 48 (1987), 170–176. The rats are decapitated and their cortex is removed, homogenized in 9 volumes of a 0.32 M sucrose buffer, buffered to pH 7.4 with 5 mM of HEPES, then centrifuged at 800 g for 20 minutes. The supernatants are recovered and the pellets are washed twice with the 0.32 M sucrose buffer as previously. The collected supernatants are centrifuged at 10000 g for 20 minutes. The pellets obtained are suspended in a Tris buffer (50 mM Tris, 130 mM NaCl, 5 mM KCl, 0.5 mM EGTA, 1 mM $MgCl_2$, pH 7.4) and centrifuged at 10000 g for 20 minutes. This stage is repeated twice, and the final pellet, corresponding to the mitochondrial fraction, is stored at −80° C. in the Tris buffer. The proteinic content of the preparation is determined by the Lowry method.

b) Bond of [$^3$H]Ro 19-6327

100 μl of the mitochondrial preparation (2 mg protein/ml) is incubated for 1 hour at 37° C. in an Eppendorf tube, in the presence of 100 μl of [$^3$H]Ro 19-6327 (33 nM, final concentration) and 100 μl of Tris buffer containing or not containing the inhibitors. The reaction is stopped by the addition of 1 ml of unlabelled Tris buffer into each tube, then the samples are centrifuged for 2 minutes at 12000 g. The supernatants are drawn off and the pellets washed with 1 ml of Tris buffer. The pellets are then solubilized in 200 μl of sodium dodecyl sulphate (20% weight/volume) for 2 hours at 70° C. The radioactivity is determined by counting the samples using liquid scintillation.

c) Results

The compound of Example 1 described above shows an $IC_{50}$ lower than 25 μM.

What is claimed is:

1. A method of treating schizophrenia, depression, psycose, disorders of the memory and the humour in warm-blooded animals comprising administering to warm-blooded animals in need thereof an amount of a compound of the formula

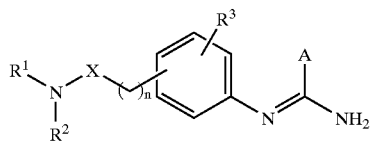

(I)

wherein $R^1$ is hydrogen or alkyl, $R^2$ is selected from the group consisting of cycloalkyl, alkenyl, alkynyl, allenyl, allenylalkyl, cyanoalkyl, and —$(CH_2)_g$—$Z^1R^4$, $Z^1$ is selected from the group consisting of —O—, $NR^6$, —S— and a bond, $R^4$ is selected from the group consisting of alkenyl, allenylalkyl, alkynyl, and cyanoalkyl, $R^6$ is hydrogen or alkyl, or $R^1$ and $R^2$ together with the nitrogen atom form a non-aromatic heterocycle with 4 to 8 members, the elements of the chain being selected from the group consisting of —CH($R^9$)—, —$NR^{10}$—, —O—, —S— and —CO—, said heterocycle being substituted by at least one —$(CH_2)_k$—$Z^2R^{11}$ or —$(CH_2)_k$—$COR^{12}$, $Z^2$ is selected from the group consisting of —O—, $NR^{13}$—, —S— and a bond, $R^{11}$, each time that it occurs is independently selected from the group consisting of alkenyl, alkynyl, allenyl, allenylalkyl and cyanoalkyl, $R^{13}$, each time that it occurs is independently hydrogen or alkyl, $R^{12}$, each time that it occurs is —$NR^{14}R^{15}$, $R^{14}$ and $R^{15}$, each time that they occur, are independently selected from the group consisting of hydrogen, alkyl, allenyl, allenylalkyll, alkenyl, alkynyl and cyanoalkyl, $R^9$ and $R^{10}$, each time that they occur, are hydrogen, X is —CO or —$(CH_2)_m$—;

$R^3$ is hydrogen, alkyl or alkoxy of 1 to 6 carbon atoms;

A is alkyl of 1 to 6 carbon atoms or a carbocyclic or heterocyclic aryl with 5 or 6 members containing 1 to 4 heteroatoms selected from the group consisting of —O—, S and —N, said aryl unsubstituted or substituted by at least one member of the group selected from the group consisting of alkyl, alkenyl and alkoxy of up to 6 carbon atoms, g, each time that is occurs, is independently, an integer from 1 to 6, m, k and n, each time that they occur, are independently, integers from 0 to 6;

it being understood however that, when $R^3$ is hydrogen or alkyl of 1 to 6 carbon atoms, then $R^1$ and $R^2$ do not represent, independently, hydrogen or alkyl, and moreover —$NR^1R^2$ do not represent one of the unsubstituted piperidynyl, morpholinyl, pyrrolidinyl groups or piperazinyl optionally substituted in position 4 by alkyl of 1 to 6 carbon atoms;

or of a pharmaceutically acceptable salt thereof sufficient to treat said conditions.

2. The method of claim 1 wherein $R^1$ is alkyl and $R^2$ is selected from the group consisting of cycloalkyl, alkenyl, alkynyl, allenyl, allenylalkyl, cyanoalkyl, and —$(CH_2)_g$—$Z^1R^4$;

$Z^1$ is selected from the group consisting of —O—, —$NR^6$—, —S— and a bond, $R^4$ is selected from the group consisting of alkenyl, alkynyl, allenylalkyl and cyanoalkyl, $R^6$ is hydrogen or alkyl, or $R^1$ and $R^2$ together with the nitrogen atom form a non-aromatic heterocycle with 4 to 8 members, the elements of the ring are selected from the group consisting of —(CH($R^9$)—, —$NR^{10}$—O—, —S— and —CO—, said heterocycle being substituted by at least one —$(CH_2)_k$—$Z^2R^{11}$ or —$(CH_2)_k$—$COR^{12}$, $Z^2$ is selected from the group consisting of —O—, $NR^{13}$—, —S— and a bond, $R^{11}$ each time that it occurs is independently selected from the group consisting of alkenyl, alkynyl, allenyl, allenylalkyl and cycanoalklyl $R^{13}$, each time that it occurs is independently hydrogen or alkyl, $R^{12}$, each time that it occurs, is $NR^{14}R^{15}$, $R^{14}$ and $R^{15}$, each time that they occur, are independently selected from the group consisting of hydrogen, alkyl, allenyl, allenylalkyl, alkenyl, alkynyl and cyanoalkyl, $R^9$ and $R^{10}$, each time that they occur, are hydrogen, k is an integer from 1 to 6; and X is —$(CH_2)_m$— with m representing 0 or 1.

3. The method of claim 1, wherein:

$R^1$ is alkyl and $R^2$ is selected from the group consisting of alkenyl, alkynyl, allenyl and cyanoalkyl, or $R^1$ and $R^2$ together with the nitrogen atom form a non-aromatic heterocycle with 4 to 8 members, the elements of the ring are —$CH(R^9)$—, —$NR^{10}$ and —O—, $R^9$ and $R^{10}$ are halogen, n is 0 or 1;

k is an integer from 1 to 3; and

X is —$(CH_2)_m$— and m is 9 or 1.

4. The method of claim 1, wherein the compound is:

N'-(4-{[methyl-(2-propynyl)amino]methyl}phenyl)-2-thiophenecarboximidamide;

N'-(4-{[methyl(cyanomethyl)amino]methyl}phenyl)-2-thiophenecarboximidamide;

N'-(4-{[methyl(3-cyanoethyl)amino]methyl}phenyl)-2-thiophenecarboximidamide;

N'-(4-{[methyl(4-pentynyl)amino]methyl}phenyl)-2-thiophenecarboximidamide;

or a pharmaceutically acceptable salt thereof.

5. The method of claim 1 wherein $R^1$ is hydrogen or alkyl and $R^2$ is selected from the group consisting of cycloalkyl, alkenyl, alkynyl, allenyl, allenylalkyl and cyanoalkyl.

6. The method of claim 1 wherein $R^1$ is hydrogen or alkyl and $R^2$ is selected from the group consisting of alkenyl, alkynyl, allenyl, allenylalkyl and cyanoalkyl.

* * * * *

UNITED STATES PATENT AND TRADEMARK OFFICE
CERTIFICATE OF CORRECTION

PATENT NO.  : 6,770,669 B1
DATED       : August 3, 2004
INVENTOR(S) : Chabrier De Lassauniere et al.

It is certified that error appears in the above-identified patent and that said Letters Patent is hereby corrected as shown below:

Title page,
Item [57], ABSTRACT,
Please replace the Abstract with the following Abstract of the Disclosure:

ABSTRACT OF THE DISCLOSURE

A method of inhibiting NO syntheses and monoamine oxydases in warm-blooded animals comprising administering to warm-blooded animals in need thereof an amount of a compound of the formula

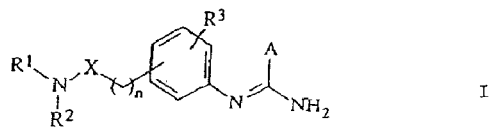

I wherein $R^1$ and $R^2$ are independent, selected from the group consisting of hydrogen, alkyl, cycloakyl, alkenyl, alkynyl, allenyl, allenylalkyl, cyanoalkyl, $-(CH_2)_g-Z^1R^4$ and $-(CH_2)_k-COR^5$, $Z^1$ is selected from the group consisting of $-O-$, $-NR^6$, $-S-$ and a bond, $R^4$ and $R^6$ are independently selected from the group consisting of hydrogen, alkyl, alkenyl, allenylalkyl, alkynyl, alkoxy and cyanoalkyl, $R^5$ is selected from the group consisting of alkyl, allenyl, allenylalkyl, alkenyl, alkynyl, cyanoalkyl, alkoxy and $-NR^7R^8$, $R^7$ and $R^8$ are independently selected from the group consisting of hydrogen, alkyl, allenyl, allenylalkyl, alkenyl, alkynyl, cyanoalkyl and alkoxy, or $R^1$ and $R^2$ together with the nitrogen atom form a non-aromatic heterocycle with 4 to 8 members, the elements of the chain being selected from the group consisting of $-CH(R^9)-$, $-NR^{10}-$, $-O-$, $-S-$ and $-CO-$, said heterocycle unsubstituted or substituted by at least one $-(CH_2)_k-Z^2R^{11}$ or $-(CH_2)_k-COR^{12}$, $Z^2$ is selected from the group consisting of $-O-$, $NR^{13}-$, $-S-$ and a bond,

UNITED STATES PATENT AND TRADEMARK OFFICE
CERTIFICATE OF CORRECTION

PATENT NO. : 6,770,669 B1
DATED : August 3, 2004
INVENTOR(S) : Chabrier De Lassauniere et al.

It is certified that error appears in the above-identified patent and that said Letters Patent is hereby corrected as shown below:

ABSTRACT, cont'd., $R^{11}$, each time that it occurs is independently selected from the group consisting of hydrogen, alkyl, alkenyl, alkynyl, alkoxy, allenyl, allenylalkyl and cyanoalkyl, $R^{13}$, each time that it occurs is independently selected from the group consisting of hydrogen, alkyl, alkenyl, alkynyl, alkoxy, allenyl, allenylalkyl and cyanoalkyl, $R^{12}$, each time that it occurs is selected from the group consisting of alkyl, allenyl, allenylalkyl, alkenyl, alkynyl, cyanoalkyl, alkoxy and $NR^{14}R^{15}$, $R^{14}$ and $R^{15}$, each time that they occur, are independently selected from the group consisting of hydrogen, alkyl, alkoxy, allenyl, allenylalkyl, alkenyl, alkynyl and cyanoalkyl, $R^9$ and $R^{10}$, each time that they occur, are independently selected from the group consisting of hydrogen, $-(CH_2)_k-Z^3R^{16}$ and $-(CH_2)_k COR^{17}$, $Z^3$ is selected from the group consisting of -O-, $-NR^{18}-$, -S- and a bond, $R^{18}$ is independently selected from the group consisting of hydrogen, alkyl, alkenyl, allenyl, allenylalkyl, alkynyl, alkoxy and cyanoalkyl, $R^{16}$, each time that it occurs, is independently selected from the group consisting of hydrogen, alkyl, alkenyl, alkynyl, alkoxy, allenyl, allenylalkyl and cyanoalkyl, $R^{17}$, each time that it occurs, is independently selected from the group consisting of alkyl, allenyl, allenylalkyl, alkenyl, alkynyl, cyanoalkyl, alkoxy and $-NR^{19}R^{20}$, $R^{19}$ and $R^{20}$ are independently, each time that they occur, selected from the group consisting of hydrogen, alkyl, alkoxy, allenyl, allenylalkyl, alkenyl, alkynyl and cyanoalkyl, X is -CO- or $-(CH_2)_m-$;

$R^3$ is hydrogen, alkyl or alkoxy of 2 to 6 carbon atoms;

A is alkyl of 1 to 6 carbon atoms or a carbocyclic or heterocyclic aryl with 5 or 6 members containing 1 to 4 heteroatoms selected

UNITED STATES PATENT AND TRADEMARK OFFICE
CERTIFICATE OF CORRECTION

PATENT NO. : 6,770,669 B1
DATED : August 3, 2004
INVENTOR(S) : Chabrier De Lassauniere et al.

It is certified that error appears in the above-identified patent and that said Letters Patent is hereby corrected as shown below:

ABSTRACT, cont'd., from the group consisting of -O-, S and -N, said aryl unsubstituted or substituted by at least one member of the group selected from the group consisting of alkyl, alkenyl and alkoxy of up to 6 carbon atoms, g, each time that it occurs, is independently, an integer from 1 to 6, m, k and n, each time that they occur, are independently, integers from 0 to 6;

it being understood however that, when $R^3$ is hydrogen or alkyl of 1 to 6 carbon atoms, then $R^1$ and $R^2$ do not represent, independently, hydrogen or alkyl, and moreover $-NR^1R^2$ do not represent one of the unsubstituted piperidynyl, morpholinyl, pyrrolidinyl groups or piperazinyl group optionally substituted in position 4 by alkyl of 1 to 6 carbon atoms;

and a pharmaceutically acceptable salt thereof sufficient to treat said conditions.

Signed and Sealed this

Seventh Day of December, 2004

JON W. DUDAS
*Director of the United States Patent and Trademark Office*